(12) United States Patent
Ashburn

(10) Patent No.: US 8,137,956 B2
(45) Date of Patent: Mar. 20, 2012

(54) FORENSIC TEST STRIP AND METHOD FOR THE DETECTION OF SEMEN

(76) Inventor: Stephen Patrick Ashburn, Fort Meade, SD (US)

( * ) Notice: Subject to any disclaimer, the term of this patent is extended or adjusted under 35 U.S.C. 154(b) by 429 days.

(21) Appl. No.: 12/271,702

(22) Filed: Nov. 14, 2008

(65) Prior Publication Data

US 2010/0124778 A1    May 20, 2010

(51) Int. Cl.
*C12M 1/34* (2006.01)
*C12M 3/00* (2006.01)

(52) U.S. Cl. ............... 435/287.9; 435/287.7; 435/287.8; 435/4; 435/21; 435/7.4; 436/63; 422/426

(58) Field of Classification Search ............... 435/287.9, 435/287.8, 29, 21, 4, 7.4, 12, 287.7, 421, 435/430; 422/430, 421, 426; 436/63, 163, 436/903
See application file for complete search history.

(56) References Cited

U.S. PATENT DOCUMENTS

| | | | | |
|---|---|---|---|---|
| 3,002,893 | A | | 10/1961 | Babson |
| 3,616,251 | A | * | 10/1971 | Linoli et al. ............... 435/12 |
| 5,981,206 | A | * | 11/1999 | Arter et al. ............... 435/21 |
| 6,764,856 | B2 | * | 7/2004 | Holmes et al. ............... 436/86 |
| 2002/0106696 | A1 | * | 8/2002 | Bagaria ............... 435/7.2 |
| 2007/0275475 | A1 | * | 11/2007 | Liang ............... 436/165 |
| 2009/0263854 | A1 | * | 10/2009 | Jacono et al. ............... 435/29 |

OTHER PUBLICATIONS

Laumann et al. "The Social Organization of Sexuality: Sexual Practices in the United States"; University of Chicago Press: Chicago, p. 216 (1994).
Mosher et al. "Sexual Behavior and Selected Health Measures: Men and Women 15-44 Years of Age, United States, 2002," Advance Data, 362, p. 10 (2005). Also [online], [retrieved on Feb. 12, 2008]. Retrieved from the Internet <URL: http://www.cdc.gov/nchs/data/ad/ad362.pdf>.
Hooft et al, Am. J. Forensic Med. Pathol., 18, pp. 45-49 (1997).
Pilch et al, Genome Biology, 7(R40) (2006).
Tanaka et al, FEBS Lett., 571, pp. 197-204 (2004).
Babson et al, Am.J.Clin.Path., 32, pp. 88-91 (1959).
Owen et al, J.Androl., 26, pp. 459-469 (2005).
Hooft et al, Forensic Sci. Int. 1992, 53, pp. 131-133 (1992).
Beckmann et al. "Obstetrics and Gynecology, Second Edition"; Williams & Wilkins: Baltimore, p. 294 (1995).
An et al, Cancer Lett., 162, pp. 135-9 (2001).
Laux et al, "Forensic Detection of Semen III. Detection of PSA Using Membrane Based Tests: Sensitivity Issues with Regards to the Presence of PSA in Other Body Fluids," [online], [retrieved on Feb. 3, 2008]. Retrieved from the Internet <URL: http://mafs.net/pdf/forensicdetectionsemen3.pdf>.
Pang et al, Forensic Sci. Int., 169, pp. 27-31 (2007).
Machery-Nagel, "Phospatesmo KM, Test Paper for the Determination of Acid Phosphatase," [online], [retrieved on Nov. 12, 2008]. Retrieved from the Internet <URL: ftp://ftp.mn-net.com/english/Instruction_leaflets/Testpapers/90607en.pdf>.

\* cited by examiner

*Primary Examiner* — William H Beisner
*Assistant Examiner* — Danielle Henkel

(57) ABSTRACT

The present invention relates to a forensic test strip and method for the detection of semen. This strip is comprised of a paper element coated with reagents which react to the presence of acid phosphatase (AP), an enzyme found in semen, and is sandwiched between a clear plastic cover and an opaque plastic backing. This assembly is peeled apart, the paper element exposed to a source of semen, and the clear cover replaced. A positive test is characterized by a bright purple color, which easily can be seen through the clear cover. An adhesive backing is provided, which allows an investigator conveniently to affix the test strip directly to a notebook.

2 Claims, No Drawings

FORENSIC TEST STRIP AND METHOD FOR THE DETECTION OF SEMEN

FIELD OF THE INVENTION

The present invention relates to forensic chemistry. In particular, it relates to an analytical test and method thereof for the detection of semen on fabrics and other surfaces.

BACKGROUND OF THE INVENTION

Conservative statistics indicate that about 14% of women and 22% of men have had affairs sometime in their marriage [Laumann et al. "The Social Organization of Sexuality: Sexual Practices in the United States"; University of Chicago Press: Chicago, page 216, 1994]. According to a recent study by the Centers for Disease Control, about 4% of both married men and women had more than one sexual partner in the previous twelve months [Mosher et al. "Sexual Behavior and Selected Health Measures: Men and Women 15-44 Years of Age, United States, 2002," Advance Data, 362, page 10, 2005]. This figure rises to 15% in the case of unmarried couples cohabiting. These data indicate that infidelity is a significant problem in the United States, and there exists a need to objectively test spouses for sexual activity. For women, one such test is for the presence of semen.

When a man has sexual intercourse with a woman, semen is deposited into the woman's vagina. Immediately after intercourse, most of the semen flows back out, but some is retained in the vagina and slowly is discharged over a period of several days [Hooft et al, Am. J. Forensic Med. Pathol., 18, pages 45-49, 1997]. Semen has over 900 identified proteins [Pilch et al, Genome Biology, 7(R40), 2006] among which are semenogelin I and II (gel-forming proteins produced by the seminal vesicles), prostate-specific antigen (PSA, a protease which breaks down semenogelin), and acid phosphatase (which breaks down spermatozoa cell membranes) [Tanaka et al, FEBS Lett., 571, pages 197-204, 2004]. These proteins can be identified by immunochromatographic assay, which forms the principle of the PSA and semenogelin tests. Acid phosphatase can be detected by the classic test first reported by Babson et al in Am. J. Clin. Pathol., 32, pages 88-91 (1959), which forms the principle of the AP test in the present invention. This test relies on the catalytic hydrolysis of 1-naphthyl phosphate to form 1-naphthol, which in turn reacts with an aryl diazonium salt, forming an intensely colored azo dyestuff. In addition to proteins, semen also has unusually high concentrations of zinc (100-200 mg/L v. 1 mg/L in plasma) [Owen et al, J. Androl., 26, pages 459-469, 2005]. Zinc (like AP and PSA) is produced by the prostate gland and after ejaculation, 50% is bound to seminal vesicle proteins. Zinc acts to stabilize DNA inside spermatozoa, is a cofactor in enzymatic reactions and also may catalyze the gel-forming reaction between semenogelin I and II. Semen may be detected by the modified zinc test of Hooft and van de Voorde [Hooft et al, Forensic Sci. Int., 53, pages 131-133, 1992].

The semen flowing back out of a woman's vagina ("backflow") is deposited on her underwear or absorbent pad. These items conveniently can be tested with the AP test strip described in this invention. The strip also can be used to test stains on other fabrics and surfaces.

All stains on women's undergarments are not semen. In fact, asymptomatic women produce, on the average, 1.5 g of vaginal fluid per day, which typically leaves a white-to-beige stain [Beckmann et al. "Obstetrics and Gynecology, Second Edition"; Williams & Wilkins: Baltimore, page 294, 1995]. Semen stains, on the other hand are white and appear mainly just after intercourse. The next day, discharge of residual semen may not be visible at all. Thus, it is impossible to tell visually whether a suspicious stain is semen, and men must rely on analytical methods of detection such as that described in the present invention.

Other methods for semen detection have been described. Immunochromatographic test strips for PSA, first described by Yoshiki [An et al, Cancer Lett., 162, pages 135-9, 2001] are commercially available from several suppliers and have been validated for use in forensic investigations [Laux et al, online, retrieved 2008]. A similar test for semenogelin recently has been described [Pang et al, Forensic Sci. Int., 169, pages 27-31, 2007]. Test methods for acid phosphatase (AP) also have been described, for example as a test strip in U.S. Pat. No. 5,981,206 (Arter et al) and as a solution in U.S. Pat. No. 3,002,893 (Babson) and U.S. Pat. No. 6,764,856 (Holmes et al). Machery-Nagel also manufactures a test paper for the determination of AP, but they do not disclose the chemistry employed [Machery-Nagel, online, retrieved 2008].

Recently Hooft et al showed that the modified zinc test was more sensitive and specific for the detection of semen than the classic acid phosphatase test [Hooft et al, Am. J. Forensic Med. Pathol., 18, pages 45-49, 1997], although the ready availability of AP test strips may be a reason why zinc strips were not more widely adopted.

Although test methods for AP have been described, a test strip assembly which allows for the ready determination of semen, easy visualization through a transparent cover, and an adhesive backing which allows for convenient placement in a notebook has not.

SUMMARY OF THE INVENTION

The present invention comprises an analytical test strip assembly and method for the detection of semen on garments and other items. The test strip consists primarily of a paper element coated with reagents which react to the presence of acid phosphatase, an enzyme found in semen, which element is sandwiched between a clear plastic cover and an opaque plastic backing. This assembly is peeled apart, the paper element exposed to a source of semen, and the clear cover replaced. A positive test is characterized by a bright purple color, which easily can be seen through the clear cover. An adhesive backing is provided, which allows an investigator to affix the test strip directly to a notebook. This method provides for the convenient detection of semen when a suspect garment is tested less than 17 hours after intercourse.

The strip is designed to be easy to use and yields instant results. It is designed to detect traces of semen on a woman's undergarment which has been discharged after sexual intercourse, and up to 17 hours later.

The AP strips can detect semen down to a $\frac{1}{2000}$ dilution. The strips are designed to be used by men who suspect their spouse may be engaged in sexual activity outside of their relationship. It also can be used by professional investigators, and parents concerned about whether their teenage daughters are sexually active.

The preferred method for the detection of semen on fabrics is to wet the suspect area with a few drops of water, and then press an AP strip against it. A color change within 60 seconds to bright purple is a POSITIVE test.

DETAILED DESCRIPTION OF THE INVENTION

The present invention relates to an analytical test strip and method for the identification of semen in suspicious stains on garments and other items. The strip is comprised of a paper element which reacts to the presence of semen, and is sandwiched in between a clear plastic cover and an opaque plastic backing with a peel-off adhesive back. The strips are sensitive to air, light and moisture. The sandwich assembly helps to protect the sensitive paper element from air and moisture and in addition, the strips typically are packaged in a resealable, airtight, opaque pouch with desiccant.

The preferred method for analyzing fabrics is to wet the suspect area with 5-10 drops of water, and then press an AP strip against it. A color change within 60 seconds to bight purple is a POSITIVE test. An investigator then can reseal the strip, peel off the paper exposing the adhesive backing, and affix the strip to a notebook for permanent record-keeping. A specific example of the preferred method is given below:

Simple procedure
1. AP test. Place 5-10 drops of distilled or deionized water on a suspect area of the garment. Press an AP strip against it. A color change within 60 seconds to bright purple is a POSITIVE test.

Alternative procedure: place a wet cotton-tipped swab against the wetted area of the garment, wrap the garment around the swab and then press the cotton-tipped swab against an AP test strip. This procedure will avoid leaving any stains on the garment.

NOTE: latex gloves are recommended for these procedures.

The AP test strip assemblies are prepared according to a modification of the method of Babson [Babson et al, Am. J. Clin. Path., 32, pp. 88-91, 1959]. In the preferred embodiment, Machery-Nagel MN 260 Filter Paper is cut into approximately one hundred 20-mm by 40-mm strips, and placed into a 1-liter rolling drum with the following reagents: 100 mg (373 µmol) naphthyl phosphate disodium salt; 160 mg (337 µmol) Fast Blue B salt; and 500 mg (2,335 µmol) sodium dihydrogencitrate. The drum is rolled steadily for an hour, and then the strips are removed, affixed to clear polypropylene tape, and the tape affixed to white vinyl backing with peel-off adhesive. A small strip of vinyl backing also is affixed to the clear tape to act as a finger hold for opening the assembly. The strips are then cut to size and packaged in resealable aluminum pouches with desiccant. It should be noted that the reagents used to prepare the strips, as well as the strips themselves are hygroscopic and should be protected from moisture. The preferred embodiment affords users a convenient source of highly sensitive test strips for detecting acid phosphatase, and thereby semen. It is not intuitively obvious from the literature what concentration of reagents to use, or what filter paper or backing material is required to make the most sensitive test strip. The preferred method consists of holding the assembly by the plastic portion and using it to carry out a detection test for semen as described above. This scheme allows users to handle the test strips without touching the highly sensitive coated portion of the strip. The strips are validated using standard dilutions of semen, as well as testing on women's undergarments at intervals after intercourse, by which method their sensitivity can be determined. In a typical batch, the strips are found to have a detection limit of a 1/2000 dilution of semen.

By means of the preferred method, the AP strips typically can detect semen on women's undergarments which has been discharged up to 17 hours after intercourse. Garments tested closer to the time of intercourse give a more strongly POSITIVE spot test. The intensity of the spot test generally decreases linearly with time, but more rapidly after 12 hours. This observation can be attributed to the rapid denaturization of AP by the acidic pH of the vagina, among other factors. Once semen has been discharged from the vagina, the marker proteins in it, including acid phosphatase can be detected for years.

A volunteer subject typically has semen visible in her vagina 17 hours after intercourse as a white, stringy substance; however, no acid phosphatase can be detected. Thus, AP appears to become denatured by the hostile chemical environment of the vagina, in a fashion similar to egg whites when they are cooked. Denaturization causes irreversible changes to the three-dimensional structure of proteins, which structure is critical for their enzymatic function.

While the invention has been described in detail with respect to the preferred embodiments thereof, it must be understood that changes can be made within the spirit and scope of the invention. All references cited herein, including patents, books, journal articles and other published prior art are incorporated for the purpose of teaching and understanding pertinent to this invention.

I claim:

1. A test strip assembly for the detection of semen, consisting of a coated paper element consisting of filter paper having affixed to it in an approximately 1:1 molar ratio the dry reagents 1-naphthyl phosphate disodium salt and Fast Blue B salt with dry sodium dihydrogencitrate as buffer, which element reacts to the presence of semen in moist stains, and is sandwiched between a clear plastic cover consisting of polypropylene tape with a finger-hold, and an opaque vinyl backing with a peel-off adhesive back.

2. A method for the detection of semen in dried stains which have been wetted with a few drops of water using the test strip assembly in claim 1.

* * * * *